United States Patent [19]
Haddock et al.

[11] Patent Number: 5,332,753
[45] Date of Patent: Jul. 26, 1994

[54] THIAZOLE DERIVATIVES, THEIR PREPARATION AND THEIR USE AS FUNGICIDES

[75] Inventors: Ernest Haddock; Susan M. Webb, both of Kent, England

[73] Assignee: Shell Research Limited, United Kingdom

[21] Appl. No.: 938,687

[22] Filed: Sep. 1, 1992

Related U.S. Application Data

[63] Continuation of Ser. No. 560,567, Jul. 31, 1990, abandoned.

[30] Foreign Application Priority Data

Aug. 4, 1989 [GB] United Kingdom ............... 8917849

[51] Int. Cl.[5] ............... C07D 417/04; A01N 43/78
[52] U.S. Cl. ............... 514/370; 514/236.8; 514/326; 548/198
[58] Field of Search ............... 548/198; 514/370, 326, 514/236.8

[56] References Cited

U.S. PATENT DOCUMENTS 4,179,277 12/1979 Beck ............................. 71/92
4,197,306 4/1980 Harrison ....................... 548/202

OTHER PUBLICATIONS

Hassan, J. Indian Chem. Soc., 53 903 (1976), abstract only.

*Primary Examiner*—Robert Gerstl

[57] ABSTRACT

Novel fungicidal thiazole derivatives of the general formula

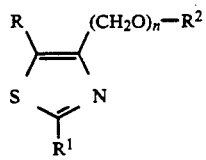

in which:
  R represents a hydrogen atom or a group of general formula —$(CH_2)_m$—Y where m is 0 or 1 and Y represents an optionally substituted nitrogen-containing heterocycle;
  $R^1$ represents a group of formula —$(CH_2)_p$—X or —N(Z)—CO—X where p is 0, 1 or 2, Z represents a hydrogen atom or an alkyl group and X represents an optionally substituted nitrogen-containing heterocycle, and, provided R represents a group in accordance with the general formula —$(CH_2)_m$—Y, may additionally represent a hydrogen atom or an optionally substituted alkyl, aryl, amino or aralkyl group;
  n is 0 or 1; and
  $R^2$ represents an optionally substituted phenyl group; and acid addition salts, N-oxides, S-oxides and metal salt complexes thereof.

15 Claims, No Drawings

THIAZOLE DERIVATIVES, THEIR PREPARATION AND THEIR USE AS FUNGICIDES

This application is a continuation of application Ser. No. 07/560,567, filed Jul. 31, 1990, now abandoned.

This invention relates to certain thiazole derivatives, to processes for their preparation and to the use of such derivatives as fungicides.

U.K. Patent Specifications Nos. 1 268 745 and 1 274 578 disclose N-benzyl imidazoles, the phenyl group being linked to the imidazole ring through a disubstituted methylene group, one of the substituents being, inter alia, a thiazolyl group. These compounds are reported as having pharmaceutical and plant growth regulating activity.

Japanese Patent Specification No J 62178590 proposes a broad range of thiazole compounds as being fungicidal and bactericidal. However, most of the compounds exemplified are substituted in the 2-position of the thiazole ring by a phenyl group. Only two compounds are substituted in the 4-position by a phenyl group, 4,5-bis(4-chlorophenyl)-2-(1-H-imidazole-1-yl)-methylthiazole (P. 611) and 4-(4-chlorophenyl)-5-(n-butyl)-2-(1-H-imidazol-1-yl) methylthiazole hydrochloride (p. 615). However, no fungicidal data is believed to be presented for these compounds.

The present invention is based upon the discovery of fungicidal activity of novel thiazole compounds which have the common characteristic of having a substituent at the 4-position of the thiazole ring, which substituent comprises a phenyl group. For many of such 4-substituted compounds which have been prepared, substantial and useful fungicidal activity has been found. In particular, the class of compounds shows consistently high activity in combating powdery mildews of cereal crops, for example *Erysiphe graminis f.sp. hordei* (barley powdery mildew).

In accordance with the present invention there is provided a thiazole derivative of the general formula I

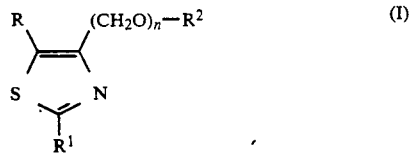

in which:

R represents a hydrogen atom or a group of general formula —(CH$_2$)$_m$—Y where m is 0 or 1 and Y represents an optionally substituted nitrogen-containing heterocycle;

R$^1$ represents a group of formula —(CH$_2$)$_p$—X or —N(Z)—CO—X where p is 0, 1 or 2, Z represents a hydrogen atom or an alkyl group and X represents an optionally substituted nitrogen-containing heterocycle, and, provided R represents a group in accordance with the general formula —(CH$_2$)$_m$—Y, may additionally represent a hydrogen atom or an optionally substituted alkyl, aryl or aralkyl group;

n is 0 or 1; and

R$^2$ represents an optionally substituted phenyl group; and acid addition salts, N-oxides, S-oxides and metal salt complexes thereof.

In general terms, unless otherwise specified in this specification, an alkyl group may be linear or branched and suitably contains up to 10, preferably up to 6, and most preferably up to 4, carbon atoms, a preferred example being methyl. An aryl group is preferably a phenyl group. A nitrogen-containing heterocyclic group is preferably a heteroaryl group, preferred groups being imidazolyl, triazolyl (such groups preferably being bonded via a N-atom) and pyridyl.

In general terms, unless otherwise stated in this specification, when any groups are designated as being optionally substituted, the substituent groups which are optionally present may be any of those customarily employed in the development of biocidal compounds, and/or the modification of such compounds to influence their structure/activity, persistence, penetration or other property. In relation to an alkyl group, including the alkyl portion of a aralkyl group, specific examples of such substituents include halogen, especially fluorine, chlorine or bromine atoms, and phenyl, cyano, amino, nitro, mono-or di-(C$_{1-4}$ alkyl)amino, C$_{1-4}$ haloalkoxy groups, and groups of the general formula MR$^7$ and C(O)MR$^7$ where M represents an oxygen or sulphur atom, R$^7$ represents a hydrogen atom, a C$_{1-8}$, especially C$_{1-4}$, alkyl group, a C$_{1-4}$ haloalkyl group or a phenyl group. In relation to an aryl or heterocyclic nitrogen-containing heterocyclic moiety, optional substituents may include halogen atoms, for example fluorine, chlorine, bromine and iodine atoms, and nitro, cyano, amino, mono or di-(C$_{1-4}$)-alkylamino, C$_{1-4}$ alkyl, C$_{2-4}$ alkenyl, C$_{2-4}$ alkynyl and C$_{1-4}$ haloalkyl (especially CF$_3$) groups, and groups of formula MR$_7$ as defined above. Such a moiety preferably has 0–3 substituents. In relation to an amino group, optional substituents may include 1 or 2 alkyl groups.

Preferably, n in general formula 1 is 0. When R$^2$ is a substituted phenyl group, preferred substituent(s) may include halogen atom(s), including chlorine, fluorine and bromine atom(s), optionally substituted (but preferably unsubstituted) phenyl group(s) alkyl, alkoxy and haloalkyl group(s), for example methyl and methoxy, nitro group(s) and cyano group(s). Particularly preferred substituent(s) may include chlorine, bromine, and fluorine atom(s), phenyl group(s), methoxy group(s) and trifluoromethyl group(s). A phenyl group having a 4-substituent (and optionally further substituents) is especially preferred, as compounds with such groups appear to have particularly high activity. A particularly preferred group —(CH$_2$O)$_n$—R$^2$ is 2,4-dichlorophenyl.

Preferably, the group Y represents a triazolyl group, preferably bonded via a nitrogen atom. Preferably, m is 1 or, most preferably, 0. It is preferred that R represents a hydrogen atom or a 1,2,4-triazol-1-yl group.

Preferably the group X may represent a N-piperidinyl group, a N-morpholino group, optionally substituted by one or more alkyl groups, or a pyridyl group, preferably bonded via a nitrogen atom; or, provided R represents a group in accordance with the general formula —(CH$_2$)$_m$—Y, may additionally represent a hydrogen atom, C$_{1-6}$ alkyl group or a phenyl, benzyl or chlorobenzyl group. Preferably Z represents an alkyl group.

Preferably, R$^1$ represents a group of formula —(CH$_2$)$_p$—X, where p is 0 or 1.

It is preferred that, when R represents a group in accordance with the general formula —$(CH_2)_m$—Y, that $R^1$ represents a hydrogen atom, a $C_{1-6}$ alkyl group, a pyridyl group, a phenyl group or a benzyl or chlorobenzyl group; and particularly that $R^1$ represents a hydrogen atom or a $C_{1-6}$ alkyl group.

Compounds of the present invention are accessible by a series of related methods, which have in common the reaction of a thio-amine compound S=C($T^1$)—$NH_2$ (II), where $T^1$ may be, for example, a hydrogen atom, or an optionally substituted alkyl or amino group, with an acetophenone compound

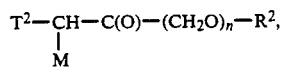  (III)

where M represents a leaving group, typically an iodine or bromine atom, and $T^2$ may represent, for example, a hydrogen atom, or an alkyl group or a heterocyclic group. The resulting compound may be a compound of general formula I, or it may itself be an intermediate compound which is derivatised to form a compound of general formula I.

Suitably, the reaction between compounds of general formula II and III is carried out in the presence of an inert organic solvent, suitably an alcohol, for example ethanol. A suitable temperature range is 20° C. to the reflux temperature. It is particularly advantageous, for achievement of a high yield, that the reaction initially be carried out in N,N-dimethylformamide, suitably at a temperature in the range 0°–50° C., conveniently ambient temperature, followed by removal of the solvent, addition of ethanol, and heating thereof, conveniently under reflux.

Within the above general scheme, particularly convenient methods for synthesizing compounds of general formula I will now be described.

when R represents a group Y:

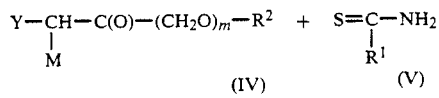

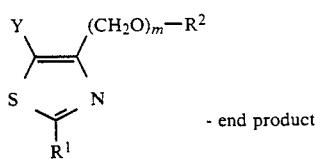
- end product where M represents a leaving group. The compound of general formula IV may be prepared by introducing leaving group M into a compound

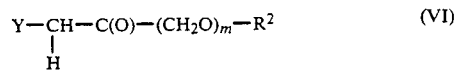  (VI)

For example, when M is a bromine atom, bromination may be carried out with, for example, a brominating agent such as N-bromosuccinimide, suitably with irradiation, in the presence of a catalyst, or by use of bromine under acidic conditions, for example in the presence of sodium acetate and acetic acid. For detailed experimental write-ups exemplifying this method, see Examples 1, 2, 3 and 7 hereunder.

when represents a group —$(CH_2)_m$—Y where m is 1 or 2:

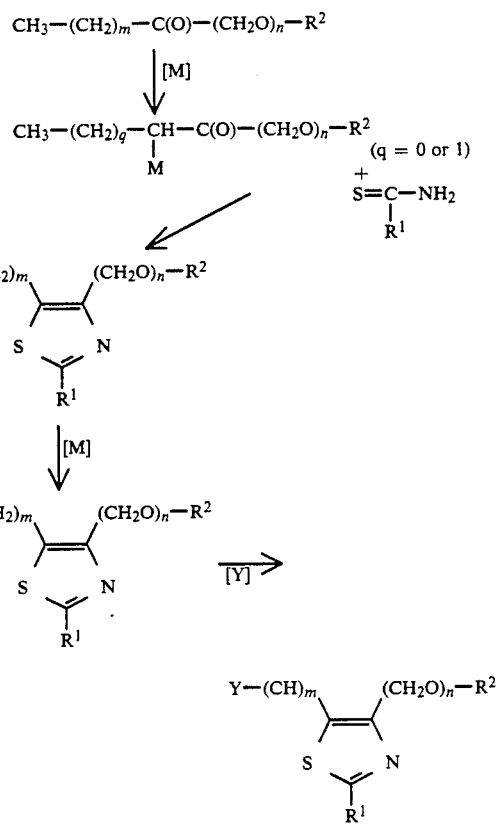

For a detailed experimental write-up exemplifying this method, see Example 5 hereunder.

when $R^1$ represents a group —$(CH_2)_p$—X where p is 1 or 2:

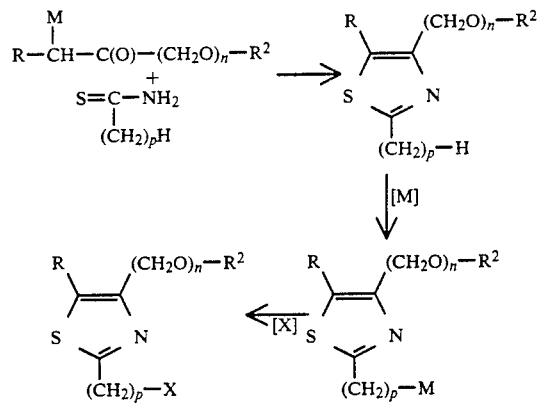

For a detailed experimental write-up exemplifying this method, see Example 4.

when an imidazolyl group X or Y is required, it may be derived from the corresponding formula I compound in which X or Y is a hydrazine group, by treatment with Gold's reagent. For a detailed experimental write-up exemplifying this method, see Example 5 hereunder.

when $R^1$ represents a group —N(Z)—CO—X a formula I compound wherein $R^1$ is —NHZ is prepared, followed by reaction with a compound X—CO—X or X—CO—Hal (especially X—CO—Cl). For a detailed experimental write-up exemplifying this method, see Example 41 hereunder.

a compound of formula I in which n is 1 may be derived following preparation of an intermediate of formula III. The latter may be achieved by reaction of a phenol R²—OH with an epoxy compound

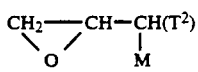

followed by oxidation of the resulting alcohol.

Further in accordance with the invention there is provided a fungicidal composition which comprises a carrier and, as active ingredient, at least one compound of general formula I as defined above.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural silicas such as diatomaceous earths; magnesium silicates, for example talcs; magnesium aluminum silicates, for example attapulgites and vermiculites; aluminum silicates, for examples kaolinites, montmorillonites and micas; calcium carbonate; calcium sulphate; synthetic hydrated silicon oxides and synthetic calcium or aluminum silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethylene. Mixtures of different liquids are often suitable. Fungicidal compositions are often formulated and transported in a concentrated form which is subsequently diluted by the user before application. The presence of small amounts of a carrier component which is a surface-active agent facilitates this process of dilution. Thus, preferably at least one carrier component in a composition according to the invention is a surface-active agent. For example, the composition may contain at least two carrier components, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecyl benzene sulphonate; and polymers of ethylene oxide and copolymers of ethylene oxide propylene oxide.

The composition of the invention may for example be formulated as wettable powders, dusts, granules, solutions, emulsifiable concentrates, emulsions, suspension concentrates and aerosols. Wettable powders usually contain 25, 50 or 75% by weight of active ingredient and usually contain, in addition to solid inert carrier, 3–10% by weight of dispersing agent and, where necessary, 0–10% by weight of stabilizer and/or other additives such as penetrants or stickers. Dusts are usually formulated as a dust concentrate having a similar composition to that of a wettable powder but without a dispersant, and may be diluted in the field with further solid carrier to give a composition usually containing 0.5–10% by weight of active ingredient. Granules are usually prepared to have a size between 10 and 100 BS mesh (1.676–0.152mm), and may be manufactured by agglomeration or impregnation techniques. Generally, granules will contain 0.5–254 by weight active ingredient and 0–10% by weight of additives such as stabilisers, slow release modifiers and binding agents. Emulsifiable concentrates usually contain, in addition to a solvent and, when necessary, co-solvent, 1–504 w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% by weight of active ingredient, 0.5–15% by weight of dispersing agents, 0.1–10% by weight of suspending agents such as protective colloids and thixotropic agents, 0–10% by weight of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also be within the scope of the present invention. The said emulsions may be of the water-in-oil type or of the oil-in-water type, and may have a thick "mayonnaise"-like consistency.

The compositions of the invention may also contain other ingredients, for example other compounds possessing pesticidal, especially insecticidal, acaricidal, herbicidal or fungicidal, properties.

Of particular interest in enhancing the duration of the protectant activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of the general formula I as defined above or a salt thereof, and a method for combating fungus at a locus, which comprises treating the locus, which may, for example, be plants subject to or subjected to fungal attack, seeds of such plants or the medium in which such plants are growing or are to be grown, with such a compound.

The present invention is of wide applicability in the protection of crop plants against fungal attack. Typical crops which may be protected include vines, grain crops such as wheat and barley, rice, beans and apples. The duration of protection is normally dependent on the individual compound selected, and also a variety of external factors, such as climate, whose impact is normally mitigated by the use of a suitable formulation. Application rates may typically be in the range 0.1 to 10 Kg active ingredient per hectare (kg/ha), preferably 0.1 to 1 kg/ha.

The invention is further illustrated by the following examples.

EXAMPLE 1

2-Methyl-4-(4'-methylphenyl)-5-(1,2,4-triazol-1-yl)-thiazole a) 2-Bromo-4'-methylacetophenone (12.78 g; 0.06 mole), sodium triazole (5.46 g; 0.06 mole) in dry acetonitrile solution (100 ml) were stirred at 20° C. for 5 hours. The solvent was evaporated and the residue purified by chromatography using silica gel/chloroform to give 2-(1,2,4-triazol-1- yl)-4'-methylacetophenone as a white solid (mp 118.4° C.). The latter compound (3.0 g; 0.015 mole) together with sodium acetate (1.23 g; 0.015 mole) and acetic acid (30 ml), was stirred at 40° C. during the addition of bromine (2.38 g; 0.015 mole) in acetic acid (2 ml). The mixture was stirred for a further 30 minutes and poured into chloroform (50 ml) and washed with water and sodium bicarbonate solution. The chloroform layer was separated, dried (MgSO4) and evaporated to give crude 2-bromo-2-(1,2,4-triazol-1-yl)-4'-methylacetophenone.

b) The crude product from a) above was dissolved in ethanol (20 ml) and added to a solution of thioformamide (0.61 g; 0.01 mole) in ethanol (20 ml) and the mixture stirred for 16 hours. The solvent was evaporated, chloroform (50 ml) was added and the mixture washed with sodium bicarbonate solution. The chloroform layer was separated, dried (MgSO4) and evaporated and the residue purified by chromatography using silica gel/chloroform/hexane to give 2-methyl-4-4'-methylphenyl -5-(1,2,4-triazol-1- yl)-thiazole (1.11 g; 29%). m.p. 102° C.

| Analysis: | Calc. %: | C 60.9 | H 4.7 | N 21.9 |
| --- | --- | --- | --- | --- |
| | Found %: | C 60.8 | H 4.9 | N 21.5 |

EXAMPLE 2

4-(2',4'-Dichlorophenyl)-5-(1,2,4-triazol-1-yl-methyl) thiazole

To 2',4'-dichloropropiophenone (2.03 g; 0.01 mole) in methylene chloride (20 ml) was added excess bromine in methylene chloride (10 ml) dropwise at 20° C. The methylene chloride layer was washed with sodium sulphite solution and water, separated, dried (MgSO4) and evaporated. The residue was dissolved in ethanol (20 ml) and thioformamide (0.61 g; 0.01 mole) was added and the mixture stirred at 20° C. for 16 hours to give 4-(2',4'-dichlorophenyl)-5-methylthiazole hydrobromide (1.72 g; 53%).

The product was neutralised and the free thiazole was treated with N-bromosuccinimide in refluxing carbon tetrachloride for 16 hours with irradiation by a lamp to give 4-(2',4'-dichlorophenyl)-5-bromomethyl thiazole The crude product was dissolved in dry acetonitrile, sodium triazole (0.91 g; 0.01 mole) was added and the mixture stirred for 16 hours at 20° C. to give, after chromatography using silica gel/chloroform: 2% ethanol, the title compound (0.71 g; 23%). m.p. 120°–123° C.

| Analysis: | Calc. %: | C 46.3 | H 2.6 | N 18.0 |
| --- | --- | --- | --- | --- |
| | Found %: | C 46.1 | H 2.7 | N 17.6 |

EXAMPLE 3

2-t-Butyl-4-(2',4'-dichlorophenyl)-5-(1,2,4-triazol-1-yl)

2-Bromo-2-(1,2,4-triazol-1- yl)-2',4'-dichloroacetophenone (12.6 g; 0.038 mole) was stirred with one molar equivalent of t-Bu-C(S)-NH2 (4.45 g; 0.038 mole) in dimethylformamide (200 ml) at ambient temperature (c. 20° C.) overnight. The dimethylformamide was removed by evaporation and ethanol (200 ml) was added. The mixture was heated under reflux overnight (c. 78° C. ). The ethanol was removed by evaporation and the residue taken up into chloroform (200 ml), washed with water, dried, and the solvent removed by evaporation. The crude product was purified by chromatography on a silica gel column eluted with dichloromethane, yielding the title compound in 66% yield as a yellow oil (8.55 g).

| Analysis: | Calc. %: | C 51.0 | H 4.2 | N 15.3 |
| --- | --- | --- | --- | --- |
| | Found %: | C 51.0 | H 4.0 | N 15.9 |

The following further compounds set forth in Table 1 below were made using processes analogous to those described in Examples 1 to 3.

TABLE 1

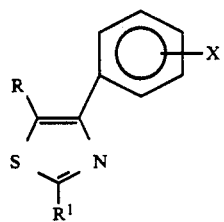

| Compound of Example No. | R | R¹ | X | m.p. (°C.) | Analysis (%) Found (Calc.) | | |
|---|---|---|---|---|---|---|---|
| | | | | | C | H | N |
| 4 | 1-(1,2,4-triazolyl) | Me | H | 91 | 59.6 (59.5) | 4.2 (4.2) | 23.3 (23.1) |
| 5 | 1-(1,2,4-triazolyl) | H | H | 113 | 57.5 (57.9) | 3.7 (3.5) | 24.2 (24.5) |
| 6 | 1-(1,2,4-triazolyl) | Me | 4-Ph | 124 | 67.1 (67.9) | 4.4 (4.4) | 16.8 (17.6) |
| 7 | 1-(1,2,4-triazolyl) | H | 4-Ph | 160 | 66.8 (67.1) | 3.9 (4.0) | 18.2 (18.4) |
| 8 | 1-(1,2,4-triazolyl) | Me | 4-Br | 119–120 | 44.9 (44.9) | 2.9 (2.8) | 17.3 (17.4) |
| 9 | 1-(1,2,4-triazolyl) | H | 4-Br | 101 | 43.1 (43.0) | 2.3 (2.3) | 18.3 (18.2) |
| 10 | 1-(1,2,4-triazolyl) | Me | 4-OMe | 99–100 | 57.3 (57.3) | 4.4 (4.4) | 20.3 (20.6) |
| 11 | 1-(1,2,4-triazolyl) | H | 4-OMe | 123 | 55.2 (55.8) | 3.8 (3.9) | 21.2 (21.7) |
| 12 | 1-(1,2,4-triazolyl) | Me | 2,3,4-triCl | 99–100 | 41.2 (41.7) | 1.8 (2.0) | 15.9 (16.2) |
| 13 | 1-(1,2,4-triazolyl) | H | 2,3,4-triCl | 118 | 39.9 (39.8) | 1.7 (1.5) | 16.7 (16.9) |
| 14 | 1-(1,2,4-triazolyl) | Me | 4-CF₃ | 96–97 | 50.2 (50.3) | 3.1 (2.9) | 17.9 (18.1) |
| 15 | 1-(1,2,4-triazolyl) | Me | 4-NO₂ | 129 | 50.2 (50.2) | 3.1 (3.2) | 23.7 (24.4) |
| 16 | 1-(1,2,4-triazolyl) | Me | 4-CN | 143 | 58.2 (58.4) | 3.4 (3.4) | 25.8 (26.2) |
| 17 | 1-(1,2,4-triazolyl) | Me | 2,4-(OMe)₂ | 173.3 | 55.7 (55.6) | 4.8 (4.7) | 18.5 (18.5) |
| 18 | 1-(1,2,4-triazolyl) | Me | 3,4-(OMe)₂ | 118.6 | 55.8 (55.6) | 4.7 (4.7) | 18.5 (18.5) |
| 19 | 1-(1,2,4-triazolyl) | Et | 2,4-diCl | 65–66 | 47.6 (48.0) | 3.1 (3.1) | 17.0 (17.2) |
| 20 | 1-(1,2,4-triazolyl) | Ph | 2,4diCl | 103 | 54.6 (54.7) | 2.8 (2.7) | 15.0 (15.0) |
| 21 | 1-(1,2,4-triazolyl) | benzyl | 2,4-diCl | 87 | 55.2 (55.8) | 3.1 (3.1) | 14.4 (14.5) |
| 22 | 1-(1,2,4-triazolyl) | —CH₂-(2',4'-dichlorophenyl) | 2,4-diCl | 118 | 47.2 (47.4) | 2.2 (2.2) | 12.2 (12.3) |
| 23 | H | —CH₂—N(piperidinyl) | H | 67 | 69.0 (69.7) | 6.8 (7.0) | 10.7 (10.8) |
| 24 | H | —CH₂—N(2,6-dimethylmorpholinyl) | 2,4-diCl | 77–82 | 53.7 (53.8) | 5.1 (5.1) | 7.9 (7.8) |
| 25 | H | —CH₂—N(piperidinyl) | 2,4-diCl | 100.5 | 55.2 (55.0) | 5.0 (4.9) | 8.7 (8.6) |

TABLE 1-continued

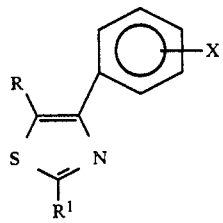

| Compound of Example No. | R | R¹ | X | m.p. (°C.) | Analysis (%) Found (Calc.) | | |
|---|---|---|---|---|---|---|---|
| | | | | | C | H | N |
| 26 | 1-(1,2,4-triazolyl) | Cl—⌬—Cl (3,4-diCl phenyl) | 2,4-diCl | 181–2 | 46.2 (45.9) | 1.8 (2.0) | 12.7 (12.6) |

EXAMPLE 27

2-(1,3-Imidazol-1-yl carbonyl-n-propylamido)-4-(2,4,6-trichlorophenoxy)-methyl-1,3-thiazole 2,4,6-Trichlorophenol (19.75 g, 0.1 mole), piperidine (0.2 g) and epichlorohydrin (27.0 g, 0.3 mole) were mixed and heated at 100° C. for 4 hours. The excess epichlorohydrin was distilled off and the residue was dissolved in chloroform (200 ml). The chloroform solution was washed with concentrated hydrochloric acid (10 ml), water (200 ml) and dried (sodium sulphate). The chloroform was evaporated and the residue distilled (126° C./0.15 mmHg) to give white crystals (22.87 g, 79%), mp 28°–30° C., of 1-chloro-3-(2,4,6-trichlorophenoxy)-propan-2-ol.

The above alcohol (3.0 g, 0.01 mole) was dissolved in acetone (50 ml) and cooled to 5°–10° C. Jones' reagent (chromium trioxide/aqueous sulphuric acid) (8 mls) was added dropwise and the mixture stirred at 20° C. for 16 hours. The mixture was filtered and the acetone filtrate evaporated. The residue was dissolved in chloroform (100 ml) and the chloroform washed with water (50 ml), dried (sodium sulphate), and evaporated. The residue was purified by chromatography using silica gel/methylene dichloride to give 1-chloro-3—(2,4,6-trichlorophenoxy)-propan-2-one as white crystals (2.76 g, 92%), mp 55° C.

The above ketone (2.88 g, 0.01 mole) and n-propylthiourea (1.18 g, 0.01 mole) in ethanol (50 ml) were refluxed (78° C.) for 2 hours. The solvent was evaporated and the residue dissolved in chloroform ml). The chloroform was washed with sodium bicarbonate solution and water and separated, dried (sodium sulphate) and evaporated. The residue was purified by chromatography using silica gel/chloroform to give white crystals (4.83 g, 95%), mp 111° C. of 2-(n-propylamino)-4-(2,4,6-trichlorophenoxy)methyl-1,3-thiazole.

| Analysis: | Calc. %: | C 44.4 | H 3.7 | N 8.0 |
|---|---|---|---|---|
| | Found %: | C 44.5 | H 3.9 | N 8.0 |

The above amine (1.0 g) and carbonyldiimidazole (1.0 g) in methylene dichloride (50 ml) were stirred at 20° C. for 70 hours. The mixture was washed with water, dried (sodium sulphate) and evaporated. The residue was purified by chromatography using silica gel/methylene dichloride to give the title compound as white crystals (1.17 g, 92%), mp 76°–77° C.

| Analysis: | Calc. %: | C 45.8 | H 3.4 | N 12.6 |
|---|---|---|---|---|
| | Found %: | C 46.1 | H 3.5 | N 12.7 |

EXAMPLE 28

2-(N—(n-propyl)-5-bromonicotinamido)-4-(2,4,6-trichlorophenoxy)methyl-1,3,-thiazole Using a method analogous to that described in Example 27, the title compound was prepared (0.96 g, 64%), mp 102° C.

| Analysis: | Calc. %: | C 42.6 | H 2.8 | N 7.8 |
|---|---|---|---|---|
| | Found %: | C 42.6 | H 3.1 | N 8.0 |

EXAMPLE 29

2- (N-(n-propyl)nicotinamido)-4-( 2,4,6,-trichlorophenoxy) methyl- 1,3-thiazole Using a method analogous to that described in Example 27, the title compound was prepared (0.65 g, 50%), mp 81° C.

| Analysis: | Calc. %: | C 50.0 | H 3.5 | N 9.2 |
|---|---|---|---|---|
| | Found %: | C 50.0 | H 3.7 | N 9.3 |

EXAMPLE 30

2-(Pyrid-3-yl)-4-(2,4,6-trichlorophenoxy)methyl-1,3-thiazole

Using a method analogous to that described in Example 27, but employing thionicotinamide in place of n-propylthiourea, there was prepared the title compound (1.3 g, 70%).

| Analysis: | Calc. %: | C 48.5 | H 2.4 | N 7.5 |
|---|---|---|---|---|
| | Found %: | C 48.4 | H 2.6 | N 7.6 |

EXAMPLE 31

2-[2-(2,6-dimethylmorpholino)ethyl]-4-(4-chlorophenyl) 1,3-thiazole -cis isomer 3-Bromopropionitrile (4.06 g, 0.03 mole), cis/trans-2,6-dimethylmorpholine (4.0 g, 0.034 mole), triethylamine (5.0 ml) and ethanol (50 ml) were refluxed (78° C.) for 3 hours and left stirring at 20° C. for 17 hours. The solvent was evaporated and the residue purified by chromatography using silica gel/chloroform: 5% methanol to give cls/trans N-(2-cyanoethyl)-2,6-dimethylmorpholine (4.0 g, 79%) as a colourless oil.

The above oil (1.0 g, 0.06 mole) was dissolved in pyridine (20ml) containing triethylamine (1.0 ml) and hydrogen sulphide gas was passed through the stirred mixture at 20° C. for 70 hours. The solvent was evaporated and the residue dissolved in chloroform (50 ml). The chloroform was washed with water, dried (sodium sulphate) and evaporated. The reside was purified by chromatography using silica gel/chloroform to give both cis(0.3 g, 25%)and trans (0.1 g, 8%) isomers of 3-(2,6-dimethylmorpholino) thiopropionamide.

The above cis isomer (0.3 g, 0.00 15 mole) was stirred at 20° C. in acetonitrile (10 ml) in the presence of 2-bromo-4'-chloroacetophenone (0.345 g, 0.0015 mole) for 70 hours. The solvent was evaporated and the residue treated with dry diethyl ether (10 ml) to give a solid which was treated with sodium bicarbonate solution to give the title compound (0.035 g, 7%).

EXAMPLE 32

Fungicidal Activity

The fungicidal activity of compounds of the invention was investigated by means of the following tests.

(a) Direct Protectant Activity Against Vine Downy Mildew (*Plasmopara viticola*; Pvp)

The test is a direct protectant one, using a foliar spray. The lower surfaces of leaves of whole vine plants (cv Cabernet Sauvignon) are sprayed with a solution of active material in 1:1 v/v water/acetone containing 0.04% w "Triton X-155" (Trade Mark) (octylphenol polyoxyethylene surfactant), at a dosage of 1 kilogram of active material per hectare using a track sprayer which delivers 620 liters/ha, and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(b) Direct Protectant Activity Against Vine Grey Mould (*Botrytis cinerea*; Bop)

The test is a direct protectant one using a foliar spray and is effected as described under (a), with the difference that the leaves are inoculated by spraying with an aqueous solution containing $10^5$ conidia/ml.

(c) Activity Against Wheat Leafspot (*Leptosphaeria nodorum*; Ln)

The test is a direct antisporulant one, using a foliar spray. Leaves of wheat plants (cv Mardler), at the single leaf stage, are inoculated by spraying with an aqueous suspension containing $8 \times 10^5$ spores/ml. The inoculated plants are kept for 24 hours in a high humidity compartment prior to treatment. The plants are sprayed at a dosage of 1 kg. of active material per hectare using a track sprayer as described under (a). After drying, the plants are kept for 5 days under normal glasshouse conditions, followed by assessment. Assessment is based on the percentage of leaf area covered by sporulation compared with that on leaves of control plants.

(d) Activity Against Barley Powdery Mildew (*Erysiphe graminis* f.sp. Hordei; Eg)

The test is a direct antisporulant one, using a foliar spray. Leaves of barley seedlings, cultivar Golden Promise, are inoculated by dusting with mildew conidia one day prior to treatment with the test compound. The inoculated plants are kept overnight at glasshouse ambient temperature and humidity prior to treatment. The plants are sprayed at a dosage of 1 kg. of active material per hectare using a track sprayer as described under (a). After drying, plants are returned to a compartment at ambient temperature and humidity for up to 7 days, followed by assessment. Assessment is based on the percentage of leaf area covered by sporulation compared with that on leaves of control plants.

(e) Activity Against Wheat Brown Rust (*Puccinia recondita*; Pr)

This test is a direct protectant one using a foliar spray. Wheat seedlings (cv Brigand) are grown to the 1–1.5 leaf stage. The plants are then sprayed with the test compound at a dosage of 1 kg/ha using a track sprayer as described under (a). Test compounds are applied as solutions or suspensions in a mixture of acetone and water (50: 50 v/v) containing 0.04% surfactant ("TWEEN 20"—Trade Mark). 18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°–22° C. Thereafter, the plants are kept in ambient glasshouse conditions, that is, in moderate relative humidity and at a temperature of 20° C. The disease is assessed 10 days after inoculation on the basis of the percentage of the plant recovered by sporulating pustules compared with that on the control plants.

(f) Activity Against Apple Powdery Mildew (*Podosphaera leucotricha*; Pl)

The test is a direct anti-sporulant one using a foliar spray. The upper surfaces of leaves of whole seedlings are inoculated by spraying with an aqueous suspension containing $10^5$ conidia/ml 2 days prior to treatment with the test compound. The inoculated plants are immediately dried and kept at glasshouse ambient temperatures and humidity prior to treatment. The plants are sprayed at a dosage of 1 kilogram of active material per hectare using a track sprayer as described under (a). After drying the plants are returned to a compartment at ambient temperature and humidity for up to 9 days, followed by assessment. Assessment is based on the percentage of the leaf area covered by sporulation compared with that on leaves of control plants.

(g) Activity Against Rice Leaf Blast (*Pyricularia oryzae*; Po)

The test is a direct eradicant one using a foliar spray. The leaves of rice seedlings (about 30 seedlings per pot) are sprayed with an aqueous suspension containing $10^5$ spores/ml 20-24 hours prior to treatment with the test compound. The inoculated plants are kept overnight in high humidity and then allowed to dry before spraying at a dosage of 1 kg of active material per hectare using a track sprayer as described under (a). After treatment the plants are kept in a rice compartment at 25°-30° C. and high humidity. Assessments are made 4-5 days after treatment and are based on the density of necrotic lesions and the degree of withering when compared with control plants.

(h) Activity Against Tomato Early Blight (*Alternaria solani*; As)

The test is a direct protectant one using a foliar spray. The upper surfaces of leaves of young tomato plants are sprayed with a solution of active material as described in (a) above. After 24 hours under normal glasshouse conditions, the upper surfaces of the leaves are inoculated by spraying with an aqueous suspension containing $10^4$ spores/ml. The inoculated plants are kept for 72 hours in a high humidity compartment and are then removed to lower humidity (50-70% relative humidity). Assessment is made 8 days after inoculation.

(i) Activity Against Wheat Eyespot (*Pseudocereosporella herpotrichoides*; Ph)

The test is an in vitro one. Samples are prepared wherein 0.7 mls solution containing 2 mg active material dissolved in acetone is evenly dispersed in 20 ml molten half-strength potato dextrose agar (formed by dissolving 2 g potato extract, 10 g dextrose and 7.5 g agar in 1 liter of water and sterilising for 15 minutes at 121° C.) and the resulting 20 ml portions are allowed to set in 9 cm petri dishes. The concentration of active material in the resulting samples is 100 ppm. Upon setting, two plugs of 5 mm diameter taken from the advancing edge of a stock plate of a 3 to 4 week old culture of *P. herpotrichoides* on full strength potato dextrose agar, incubated at 20°-22° C. in darkness, are placed, equally spaced on the surface of each sample, mycelial side uppermost. The samples are incubated for 11 days at 20°-22° C. in darkness before assessment. Diametric growth is measured with the width of the plug subtracted and results compared with growth on a sample wherein 0.7 ml acetone containing no active material is dispersed in 20 ml half-strength potato agar.

(j) Activity Against Fusarium In-Vitro (Fusarium Species; Fs)

This test measures the in vitro activity of compounds against a species of Fusarium that causes stem and root rot. The test compound is dissolved or suspended in acetone and added to molten half strength Potato Dextrose Agar to give a final concentration of 100 ppm compound and 3.5% acetone. After the agar has set, plates are inoculated with 6 mm diameter plugs of agar and mycelium taken from a 7 day old culture of Fusarium sp. Plates are incubated at 20° C. for 5 days and radial growth from the plug is measured.

(k) Antisporulant Activity Against Vine Downy Mildew (*Plasmopara viticola*; Pva)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, and then 24 hours at glasshouse ambient temperature and humidity. When the plants are dry, infected leaves are sprayed on their lower surfaces with a solution of active material in 1:1 water/acetone containing 0.04% w/w "Triton X-155" (trade mark) (an octylphenol polyethoxylate surfactant). The spraying is carried out with a moving track sprayer with delivers 620 liter/ha, and the concentration of active material is calculated to give an application rate of 1 kg/ha. After spraying, the plants are returned to normal glasshouse conditions for 96 hours and are then transferred to the high humidity compartment for 24 hours to induce sporulation, prior to assessment. Assessment is visual and is based on the percentage of the leaf area covered by sporulation compared with that on control leaves.

(l) Foot Rot of Wheat, Drench Test (*Fusarium Culmorum*; Fc)

This test measures the activity of compounds applied as a drench.

Wheat seeds (cv Waggoner) are inoculated by soaking/rolling in a concentrated spore suspension *F. colmorum* (approx. 1,500,000 spores/ml) for 2 hours. Five inoculated seeds are then sown in sand which is well watered and kept humid overnight at 20°-22° C. Compound is dissolved or suspended in 10% aqueous acetone and is applied at a rate of 5 mls per pot to give a dose rate of 10 kg/ha. Pots are kept moist and are incubated for 21 days at 25° C.

Symptoms are assessed on the roots and lower stem after plants have been removed from pots and washed. A 0-9 scale of disease is used where 0 means no disease and 9 represents the strongest development normally encountered. Activity is then converted to the 0-2 scale of control used in Primary Screens.

TABLE 2

| Compound of Example | Pvp | Po | Bcp | Ln | Eg | Pl | Pr | Pva | As | Ph | Fs | Fc |
|---|---|---|---|---|---|---|---|---|---|---|---|---|
| 1 | | | | 1 | 2 | | | | | | | |
| 2 | 1 | | | | | | | | | | | |
| 3 | 2 | | | 2 | 2 | 2 | | | 2 | 1 | | |
| 4 | | | | 2 | 1 | | 1 | | 1 | | | |
| 5 | | | | | 1 | | | | | | | |
| 6 | 1 | | | 2 | 2 | | | 2 | 1 | 1 | | |
| 7 | | | | 1 | 1 | | | | | | | |
| 8 | | | | 2 | 2 | | | | 1 | 1 | | |
| 9 | | | | 1 | 2 | | 1 | | 1 | 1 | | |
| 10 | | | | 2 | 2 | | | | 1 | | | |
| 11 | | | | 2 | | | 1 | | | | | |
| 12 | 2 | | | 2 | 2 | | | 2 | | 1 | | |
| 13 | 2 | | | | 1 | 1 | | | 1 | 1 | 1 | |
| 14 | | | | 2 | 2 | | | | | 1 | | |
| 15 | 1 | | | | 1 | | | | 2 | 1 | | |
| 16 | | | | 2 | | | | | 1 | | | |
| 17 | | | | | 1 | | | | | | | |
| 18 | | | | | 1 | 1 | | | | | | |
| 19 | | | 2 | | 1 | | 1 | | 1 | | | |
| 20 | 1 | | | 1 | 2 | | | 1 | 1 | 1 | | |
| 21 | 2 | | | 1 | 2 | 2 | | | 1 | 1 | | |
| 22 | | | 1 | 2 | | | 2 | | 1 | | | |
| 23 | | | | 1 | | | | | | | | |
| 24 | | | | | 1 | | | | | | | |
| 25 | 2 | 1 | | | 2 | | | | | | | |
| 26 | 2 | 1 | | | | | | | | | | |
| 27 | | | | | 2 | | | | | | | |
| 28 | 1 | | | | 2 | | | | | | | |

The reader's attention is directed to all papers and documents which are filed concurrently with this specification, and which are open to public inspection with this specification and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in the specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

We claim:

1. A thiazole derivative of the formula I

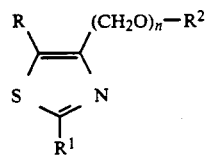

in which:

R represents a triazol-1-yl group; $R^1$ represents a hydrogen atom or a $C_{1-6}$ alkyl group; n is 0 or 1; and $R^2$ represents a phenyl group optionally substituted by up to 3 substituents selected from halogen atoms, phenyl, nitro, cyano, amino, mono- or di-($C_{1-4}$ alkyl)amino, $C_{1-4}$ alkyl, $C_{2-4}$ alkenyl, $C_{2-4}$ alkynyl, $C_{1-4}$ haloalkyl groups and groups of formula $MR$ where M represents an oxygen or sulfur atom and $R^7$ represents a hydrogen atom, $C_{1-8}$ alkyl, $C_{1-4}$ haloalkyl or phenyl group; and acid addition salts, N-oxides, S-oxides and metal salt complexes thereof.

2. A method of combating a fungus at a locus, which comprises treating the locus with an effective amount of a fungicidal composition which comprises a carrier and as active ingredient an effective amount of a compound of formula I

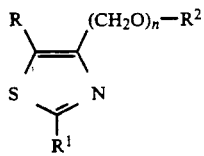

in which

R represents a hydrogen atom or a group of formula —$(CH_2)_m$—Y where m is 0 or 1 and Y represents an imidazolyl, triazolyl or pyridyl group optionally substituted by up to 3 substituents selected from halogen atoms, nitro, cyano, amino, mono- or di-($C_{1-4}$ alkyl)amino, $C_{1-4}$ alkyl, $C_{2-4}$ alkenyl, $C_{2-4}$ alkynyl, $C_{1-4}$ haloalkyl groups and groups of the formula $MR^7$ where M represents an oxygen or sulfur atom and $R^7$ represents a hydrogen atom, $C_{1-8}$ alkyl, $C_{1-4}$ haloalkyl or phenyl group; $R^1$ represents a group of formula —$(CH_2)_p$—X or —N(-Z)—CO—X where p is 0, 1 or 2, Z represents a hydrogen atom or a $C_{1-10}$ alkyl group and X represents an N-linked piperidinyl, N-liked morpholino, N-linked imidazolyl or C-linked pyridyl group each optionally substituted by up to 3 substituents selected from halogen atoms, nitro, cyano, amino mono- or di-($_{1-4}$ alkyl)amino, $C_{1-4}$ alkyl, $C_{2-4}$ alkenyl, $C_{2-4}$ alkynyl, $C_{1-4}$ haloalkyl groups, and groups of the formula $MR^7$ as defined above, and, provided R represents a group in accordance with the formula —$(CH_2)_m$—Y may additionally represent a hydrogen atom, a $C_{1-10}$ alkyl or benzyl group each optionally substituted by one or more substituents selected from halogen atoms, phenyl, cyano, amino, nitro, mono- or di-($C_{1-4}$ alkyl)amino, $C_{1-4}$ haloalkyl groups and groups of the formula $MR^7$ and $C(O)MR^7$ where M and $R^7$ are as defined above, or a phenyl group optionally substituted by up to 3 substituents selected from halogen atoms, nitro, cyano, amino, mono- or di-($C_{1-4}$ alkyl)amino, $C_{1-4}$ alkyl, $C_{2-4}$ alkenyl, $C_{2-4}$ alkynyl, $C_{1-4}$ haloalkyl groups and groups of formula $MR^7$ as defined above; n is 0 or 1; and $R^2$ represents a phenyl group optionally substituted by up to 3 substituents selected from halogen atoms, phenyl, nitro, cyano, amino, mono- or di-($C_{1-4}$ alkyl)amino, $C_{1-4}$ alkyl, $C_{2-4}$ alkenyl, $C_{2-4}$ alkynyl, $C_{1-4}$ haloalkyl groups and groups of formula $MR^7$ as defined above; and acid addition salts, N-oxides, S-oxides and metal salt complexes thereof.

3. A method of combating a fungus at a locus, which comprises treating the locus with an effective amount of a compound of formula I

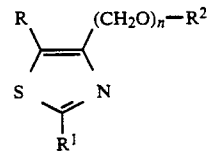

in which

R represents a hydrogen atom or a group of formula —$(CH_2)_m$—Y where m is 0 or 1 and Y represents an imidazolyl, triazolyl or pyridyl group optionally substituted by up to 3 substituents selected from halogen atoms, nitro, cyano, amino, mono- or di-($C_{1-4}$ alkyl)amino, $C_{1-4}$ alkyl, $C_{2-4}$ alkenyl, $C_{2-4}$ alkynyl, $C_{1-4}$ haloalkyl groups and groups of the formula $MR^7$ where M represents an oxygen or sulphur atom and $R^7$ represents a hydrogen atom, $C_{1-8}$ alkyl, $C_{1-4}$ haloalkyl or phenyl group; $R^1$ represents a group of formula —$(CH_2)_p$—X or —N(-Z)—CO—X where p is 0, 1 or 2, Z represents a hydrogen atom or a $C_{1-10}$ alkyl group and X represents an N-linked piperidinyl, N-linked morpholino, N-linked imidazolyl or C-linked pyridyl group each optionally substituted by up to 3 substituents selected from halogen atoms, nitro, cyano, amino mono- or di-($_{1-4}$ alkyl)amino, $C_{1-4}$ alkyl, $C_{2-4}$ alkenyl, $C_{2-4}$ alkynyl, $C_{1-4}$ haloalkyl groups, and groups of formula $MR^7$ as defined above, and, provided R represents a group in accordance with the formula $-(CH_2)_m-Y$ may additionally represent a hydrogen atom, a $C_{1-10}$ alkyl or benzyl group each optionally substituted by one or more substituents selected from halogen atoms, phenyl, cyano, amino, nitro, or mono- or di-($C_{1-4}$ alkyl)amino, $C_{1-4}$ haloalkyl groups and groups of the formula $MR^7$ and $C(O)MR^7$ where M and $R^7$ are as defined above, or a phenyl group optionally substituted by up to 3 substituents selected from halogen atoms, nitro, cyano, amino, mono- or di-($C_{1-4}$ alkyl)amino, $C_{1-4}$ alkyl, $C_{2-4}$ alkenyl, $C_{2-4}$ alkynyl, $C_{1-4}$ haloalkyl groups and groups of formula $MR^7$ as defined above; n is 0 or 1; and $R^2$ represents a phenyl group optionally substituted by up to 3 substituents selected from halogen atoms, phenyl, nitro, cyano, amino, mono- or di-($C_{1-4}$ alkyl)amino, $C_{1-4}$ alkyl, $C_{2-4}$ alkenyl, $C_{2-4}$ alkynyl, $C_{1-4}$ haloalkyl groups and groups of formula $MR^7$ as defined above; and acid addition salts, N-oxides, S-oxides and metal salt complexes thereof.

4. The method of claim 3 wherein R represents a hydrogen atom or a group of formula $-(CH_2)_m-Y$, where m is 0 and Y is as defined in claim 3.

5. The method of claim 3 wherein Y represents a triazolyl group.

6. The method of claim 3 wherein $R^1$ represents a group of formula $-(CH_2)_p-X$, wherein p is 0 or 1 and X is as defined in claim 3.

7. The method of claim 6, wherein $R^1$ represents a group of formula $-(CH_2)_p-X$ wherein p is 0 or 1 and X represents a pyridyl, piperidinyl, morpholino or methylmorpholino group, and provided R is a group in accordance with the formula $-(CH_2)_m-Y$ as defined in claim 3 may additionally represent a $C_{1-6}$ alkyl, phenyl, benzyl or chlorobenzyl group.

8. The method of claim 3 wherein R represents a triazol-1-yl group and $R^1$ represents a hydrogen atom or a $C_{1-6}$ alkyl group.

9. The method of claim 3 wherein n is 0 and $R^2$ represents a phenyl group optionally substituted by one or more substituents independently selected from halogen atoms, nitro, $C_{1-4}$ alkyl, alkoxy and haloalkyl groups, and phenyl and cyano groups.

10. The method of claim 2 wherein R represents a hydrogen atom or a group of formula $-(CH_2)_m-Y$, where m is 0 and Y is as defined in claim 9.

11. The method of claim 2 wherein Y represents a triazolyl group.

12. The method of claim 2 wherein $R^1$ represents a group of formula $-(CH_2)_p-X$, wherein p is 0 or 1 and X is as defined in claim 9.

13. The method of claim 12, wherein $R^1$ represents a group of formula $-(CH_2)_p-X$ wherein p is 0 or 1 and X represents a pyridyl, piperidinyl, morpholino or methylmorpholino group, and provided R is a group in accordance with the formula $-(CH_2)_m-Y$ as defined in claim 9 may additionally represent a $C_{1-6}$ alkyl, phenyl, benzyl or chlorobenzyl group.

14. The method of claim 2 wherein R represents a triazol-1-yl group and $R^1$ represents a hydrogen atom or a $C_{1-6}$ alkyl group.

15. The method of claim 2 wherein n is 0 and $R^2$ represents a phenyl group optionally substituted by one or more substituents independently selected from halogen atoms, nitro, $C_{1-4}$ alkyl, alkoxy and haloalkyl groups, and phenyl and cyano groups.

* * * * *